United States Patent
Benbadis et al.

(10) Patent No.: US 7,563,436 B2
(45) Date of Patent: *Jul. 21, 2009

(54) **MUTANT *LACTOBACILLUS BULGARICUS* STRAINS FREE FROM BETA-GALACTOSIDASE ACTIVITY**

(75) Inventors: Laurent Benbadis, Anthony (FR); Pierre Brignon, Strasbourg (FR); François Gendre, Strasbourg (FR)

(73) Assignee: Compagnie Gervais Danone (FR)

( * ) Notice: Subject to any disclaimer, the term of this patent is extended or adjusted under 35 U.S.C. 154(b) by 641 days.

This patent is subject to a terminal disclaimer.

(21) Appl. No.: 11/056,409

(22) Filed: Feb. 11, 2005

(65) Prior Publication Data

US 2005/0196388 A1 Sep. 8, 2005

Related U.S. Application Data

(62) Division of application No. 09/700,687, filed as application No. PCT/FR99/01165 on May 17, 1999, now Pat. No. 6,875,601.

(30) Foreign Application Priority Data

May 22, 1998 (FR) .................................. 98 06456

(51) Int. Cl.
*A61K 35/74* (2006.01)

(52) U.S. Cl. .................. 424/93.45; 424/93.4; 424/535; 435/170

(58) Field of Classification Search ............... 424/93.45, 424/93.4, 535; 435/170
See application file for complete search history.

(56) References Cited

U.S. PATENT DOCUMENTS

| 5,382,438 A | 1/1995 | Hottinger et al. |
| 5,639,648 A | 6/1997 | Mainzer et al. |
| 5,691,185 A | 11/1997 | Dickely et al. |

FOREIGN PATENT DOCUMENTS

| EP | 0 355 036 | 2/1990 |
| EP | 0 518 096 A | 12/1992 |
| JP | 02-053437 | 2/1990 |
| WO | WO 90/05459 A | 5/1990 |

OTHER PUBLICATIONS

Yoast et al., "Generation and characterization of environmentally sensitive variants of the beta-galactosidase from *L. bulgaricus*", *Applied and Environmental Microbiology*, 1994, vol. 60, No. 4, p. 1221-1226—abstract.
Mollet et al., "A beta-galactosidase deletion mutant of *L. bulgaricus* reverts to generate an active enzyme by internal DNA seq duplication", Mol Gen Genet, 1991, 227(1), 17-21—abstract.
"Genetic Engineering of Lactobacillus", *Food Technology*, Oct. 1986, No. 10.
Mollet et al., "Spontaneous Deletion Formation within the β-Galactosidase Gene of *Lactobacillus bulgaricus*", *Journal of Bacteriology*, vol. 172, No. 10, Oct. 1990, pp. 5670-5676.
Rieger et al., *Glossary of Genetics: Classical and Molecular*, pp. 348-349.
Chandan, "The Production Process", *Yogurt: Nutritional and Health Properties*.
Mainzer et al., "Pathway Engineering of *Lactobacillus bulgaricus* for Improved Yogurt", *Impact of Biotechnology on Yogurt*, pp. 41-55.

*Primary Examiner*—Ruth A Davis
(74) *Attorney, Agent, or Firm*—Alston & Bird LLP (57) ABSTRACT

The invention concerns mutant *L. bulgaricus* strains bearing a nonsense mutation, in at least one of the sequences coding for the lactose operon, and free from β-galactosidase activity, and lactic starters comprising these strains. The strains and starters can be used to obtain fermented milk products from glucose-added milk.

10 Claims, 1 Drawing Sheet

MUTANT *LACTOBACILLUS BULGARICUS* STRAINS FREE FROM BETA-GALACTOSIDASE ACTIVITY

CROSS-REFERENCE TO RELATED APPLICATIONS

This application is a divisional of Ser. No. 09/700,687, filed on Feb. 14, 2001 now U.S. Pat. No. 6,875,601, which was a national stage filing under 35 U.S.C. 371 of PCT/FR99/01165 filed May 17, 1999.

FIELD OF THE INVENTION

The present invention relates to novel variants of *bulgaricus* and to their use for preparing fermented dairy products. These strains and ferments can be used for obtaining fermented dairy products from milk supplemented with glucose.

Yogurts are conventionally obtained by fermentation of milk with a combination of *Streptococcus thermophilus* and *Lactobacillus bulgaricus*. During the fermentation, which is carried out at a temperature of approximately 40 to 45° C., these bacteria use mainly lactose as an energetic substrate, and produce lactic acid which causes the milk to coagulate; when the pH reaches a value of approximately 4.8 to 4.5, this fermentation step (also named "acidification") is terminated by cooling the product. This product is then kept in the cold during the remainder of the manufacturing and packaging process, and until its consumption.

However, the cooling does not completely stop the lactic acid fermentation; even when the product is kept at 4° C., a gradual increase in its acidity is observed over time.

This phenomenon, known as postacidification, is responsible for degradation of the organoleptic qualities of the product during its conservation.

The postacidification results essentially from the use by the bacteria, and mainly by *L. bulgaricus*, of the lactose remaining in the product at the end of the controlled acidification step. In order to avoid it, it has been proposed to use strains of *L. bulgaricus* which ferment lactose hardly or not at all.

One of the enzymes which are essential for the fermentation of lactose is β-galactosidase, which hydrolyzes lactose into glucose and galactose. It has therefore been proposed, in order to obtain non-postacidifying strains of *L. bulgaricus*, to produce artificial mutants, or to select natural mutants, in which the activity of this enzyme is affected.

For example, patent EP 402 450 in the name of GENENCOR describes the production, by localized mutagenesis of the β-galactosidase gene, of conditional mutants of *L. bulgaricus*, in which the β-galactosidase, which is active during the fermentation at 40° C., loses its activity at the temperature or at the pH corresponding to the conditions of conservation of fermented dairy products.

Application JP 90053437 describes the production of an artificial mutant of *L. bulgaricus* which has completely lost the capacity to ferment lactose, and the selection of a natural mutant with decreased lactose fermentation capacity; these mutants are however both capable of developing and acidifying normally in the presence of *S. thermophilus*, on condition that the medium is supplemented with glucose. The subcultures of these mutants conserve their acidification characteristics, in milk lacking glucose, after 10 subculturings.

Patent EP 0518 096, in the name of the SOCIÉTÉ DES PRODUITS NESTLÉ, proposes to use, for manufacturing yogurt, poorly postacidifying mutants of *Lactobacillus bulgaricus* which have been preselected on the criterion of the deletion of a fragment of the β-galactosidase gene. The screening and characterization of these mutants are facilitated due to the fact that the presence of this deletion can be easily verified on restriction profiles. In addition, the deletions are known to be irreversible mutations, which make it possible to easily obtain stable mutant strains from the parent strain. Patent EP 0518 096 describes two types of weakly postacidifying mutants selected in this way. The first have a deletion which affects only the β-galactosidase gene; when they are combined with *S. thermophilus* and cultured on milk, they exhibit, even without the addition of glucose, growth and acidification properties which are comparable to those of the wild-type strain from which they are derived. The second have a larger deletion, stretching over at least 1 kb downstream of the β-galactosidase gene; when they are combined with *S. thermophilus*, they grow more slowly and acidify much less than the wild-type strain from which they are derived; the addition of glucose to the culture medium has only a slight influence on their acidification and postacidification properties.

Natural mutants in which the β-galactosidase is inactive are much more difficult to select and to maintain as pure cultures in the case of point mutations than in the case of deletion mutants; this is explained by the lower probability of a point mutation producing an inactive protein, by the greater difficulty in localizing and characterizing the point mutations using restriction profiles, and by the very high reversion rate.

SUMMARY OF THE INVENTION

The applicant has now found other natural mutants of *L. bulgaricus*, which do not carry a deletion in the gene encoding β-galactosidase, and which have advantageous technological characteristics. In the context of the present invention, a non-sense mutant, which is incapable of assimilating lactose, has been isolated from a culture of a wild-type *L. bulgaricus*. When combined with *S. thermophilus*, in culture on milk, it grows and acidifies much more slowly than the wild-type strain from which it is derived. Conversely, its growth and its acidification are virtually normal when the milk is supplemented with glucose.

A subject of the present invention is a mutant strain of *L. bulgaricus* lacking β-galactosidase activity, characterized in that it carries a mutation which introduces a non-sense codon into one of the coding sequences of the lactose operon, and in particular the sequence encoding β-galactosidase.

A strain of *L. bulgaricus* in accordance with the invention was deposited according to the Treaty of Budapest, on Jan. 14, 1998, with the CNCM (Collection Nationale de Cultures de Microorganisms [National Collection of Microorganism Cultures]) held by the Pasteur Institute, 25 rue du Docteur Roux, in Paris, under the number I-1968.

This strain has the following morphological and biochemical characteristics:

Morphology: Gram-positive microorganism, immobile, isolated or short-chain, asporogenic, pleomorphic, thin bacilli.

Metabolism: homofermentative, catalase (−).

Fermentation of sugars: D-glucose (+), D-fructose (+), D-mannose (+), esculine (+).

The inventors have sequenced the lactose operon in the I-1968 mutant. The corresponding sequence is represented in the appended sequence listing under the number SEQ ID No: 1. The sequences of the translation products (permease and β-galactosidase) are represented under the numbers SEQ ID No: 2 and SEQ ID No: 3, respectively.

The analysis of this sequence reveals two point mutations: one, in the permease gene (position 122 of the sequence SEQ ID No: 1), induces an amino acid change (Lys→Asn); the other, in the β-galactosidase gene (position 4519 of the sequence SEQ ID No: 1), introduces a stop codon. Although conserving its active sites (positions 464 and 531), the β-galactosidase produced by this mutant is inactive. The inventors have also noted that this mutation remains stable after several series of subculturing, on a culture medium containing glucose. On the other hand, on a culture medium without glucose, this non-sense mutation reverts very rapidly at a rate of approximately $10^{-6}$.

The present invention also encompasses mutant strains which are incapable of assimilating lactose and which are derived from the I-1968 strain. Such strains can, for example, be obtained by inducing other mutations in the lactose operon of the I-1968 strain, by site-directed mutagenesis.

A subject of the present invention is also a lactic ferment, in particular a yogurt ferment, characterized in that it comprises at least one strain of L. bulgaricus in accordance with the invention as defined above, preferably combined with at least one strain of S. thermophilus.

For the production of a ferment in accordance with the invention, any strain of S. thermophilus which is suitable for manufacturing yogurt can be used; the choice of one or more strains of S. thermophilus can be made as a function of the additional characteristics that it is desired optionally to confer on the finished product.

By way of example of strains of S. thermophilus which can be used in combination with a strain of L. bulgaricus in accordance with the invention, mention may be made of the following strains, deposited with the CNCM (Collection Nationale de Cultures de Microorganismes [National Collection of Microorganism Cultures]) held by the Pasteur Institute, 25 rue du Docteur Roux, in Paris:

the strain deposited on Aug. 25, 1994, under the number I-1470, and the strain deposited on Aug. 23, 1995, under the number I-1620; these two strains are described in the European Application published under the number 96/06924;

the strains deposited on Dec. 30, 1994, under the numbers I-1520 and I-1521; these 2 strains are described in PCT international application WO 96/20607;

the strain deposited on Oct. 24, 1995 under the number I-1630; the characteristics of this strain are described in PCT international application WO 96/01701.

These strains can be combined mutually or with one or more other industrial strains of S. thermophilus.

The strain(s) of S. thermophilus is (are) combined with the strain(s) of L. bulgaricus in accordance with the invention, in the same way and in the same proportions as in conventional yogurt ferments; the population of L. bulgaricus bacteria in accordance with the invention may, for example, represent between 10 and 90%, preferably between 20 and 50%, of the total bacterial population.

A subject of the present invention is also a method for preparing a fermented dairy product, characterized in that it comprises a step during which milk is fermented using a ferment comprising at least one strain of L. bulgaricus in accordance with the invention, in the presence of at least one sugar which can be assimilated by said strain; it can be in particular fructose, mannose and, preferably, glucose. Advantageously, said fermented dairy product is a yogurt.

The method in accordance with the invention is similar to conventional methods for preparing yogurt with regard to the main methods of implementation of the controlled acidification step; in particular, this acidification is carried out at a temperature of between 20 and 45° C., and preferably between 30 and 45° C., and "batchwise", i.e. in a single step and using a single fermentation tank.

The duration of this controlled acidification step is generally about 6 to 24 hours, and preferably about 6 to 16 hours; it is therefore longer than in the case of conventional methods for preparing yogurt (in which it is 3 to 5 hours at 44° C.). Specifically, the strains of L. bulgaricus in accordance with the invention, even combined with S. thermophilus, grow and acidify much more slowly than the wild-type strains.

In addition, the rate of growth and acidification of the strains of L. bulgaricus in accordance with the invention varies very significantly depending on the amount of glucose added to the milk. This property makes it possible to control their growth and their acidification, by simply adding the desired amount of glucose at the start of fermentation.

The inventors have also observed that, when strains of L. bulgaricus or ferments in accordance with the invention are used, the acidification slows down considerably when the pH reaches the range of 4.8 to 4.5 (which corresponds to the pH range at which acidification is stopped in the case of a conventional method), and stabilizes, even if the milk is maintained at fermentation temperature, at a minimum pH. The value of this minimum pH depends essentially on the amount of glucose added.

This property makes it possible to reduce, or even to eliminate, the cooling phase used in conventional methods for manufacturing yogurt to stop the fermentation. It also eliminates the necessity of measuring the pH to determine the optimum moment for stopping the fermentation; for a given ferment and amount of added glucose, it is possible, without risk of overacidification, to stop the fermentation at the end of a given period, calculated as a function of the time required to reach the minimum pH. This makes it possible to have better control of the regularity of the final pH and of the texture for the product at the end of fermentation.

Advantageously, for the implementation of the method in accordance with the invention, and depending on the degree of acidification that it is desired to reach, the amount of glucose added to the milk prior to the fermentation is between 0.5 and 10 g/l, preferably between 0.5 and 5 g/l.

The fermented product obtained in this way can be conserved for several hours at a temperature close to the fermentation temperature, without a drop in pH, thereby making it possible to eliminate the installations for intermediate cold storage, and to increase the capacity of the fermentation tanks.

The implementation of the method in accordance with the invention makes it possible to reduce the post-acidification in the fermented products during their longer term conservation. The degree of post-acidification can vary depending on the composition of the ferment and the amount of glucose used. However, the post acidification is always clearly lower than that observed in the case of yogurts obtained with conventional ferments and methods.

For example, experiments carried out by the inventors have shown that, under the same conservation conditions (28 days of conservation at 10° C.), the OpH (difference between the pH at DO and the pH at D28) is between 0.05 and 0.4 in the case of the products obtained using a ferment in accordance with the invention, whereas it is always greater than 0.7 in the case of control ferments in which the strain of L. bulgaricus in accordance with the invention is replaced with a wild-type strain.

This weak postacidification is accompanied by good survival of the strains of the ferment; the Population of L. bulgaricus, at the end of conservation, in the fermented product obtained in accordance with the invention is only slightly smaller than that of the control product.

A subject of the present invention is also the fermented dairy products which can be obtained by implementing a method in accordance with the invention.

These products can be conserved for a longer time and at higher temperatures than the products obtained using conventional methods, and have organoleptic properties which remain stable during conservation.

EXAMPLES

Example 1

Biochemical Assaying of the Betagalactosidase Activity of a Mutant in Accordance with the Invention The (β-galactosidase activity of the I-1968 strain was compared with that of the wild-type strain of L. bulgaricus (hereafter termed LbS) from which it is derived.

The bacteria are cultured overnight on MRS agar medium (MERCK) at 37° C., in an anaerobiosis jar (MERCK) in the presence of an oxygen fixer (AnaerocultA, MERCK).

A 10-microliter loop (NUNC) of bacteria is resuspended in 1 milliliter of sterile water. The bacteria are lyzed with 2 cycles of vigorous shaking, 20 seconds at 5000 rotations per minute in the presence of glass microbeads (0.5 mm in diameter, BIOSPEC PRODUCTS), and then addition of 0.15 ml of chloroform. The mixture is shaken for 30 minutes at 37° C., and the volume is made to 2 ml with sterile water at 4° C. The beta-galactosidase activity is then measured: starting with 0.2 ml of the cell suspension, 1.2 ml of 0.067M $NaH_2PO_4$ buffer, pH 6.8; 0.05 ml of L-cysteine (SIGMA) at t0 0.05 ml of 0-nitrophenyl-beta-D-galactopyranoside (SIGMA) are added. The enzymatic reaction is stopped after 0, 2, 5 or 10 min, with 1 ml of 10% $Na_2CO_3$ buffer, and, after centrifugation of the reaction medium, a measurement of the OD at 400 nanometers is performed on the supernatant.

Figure 1:
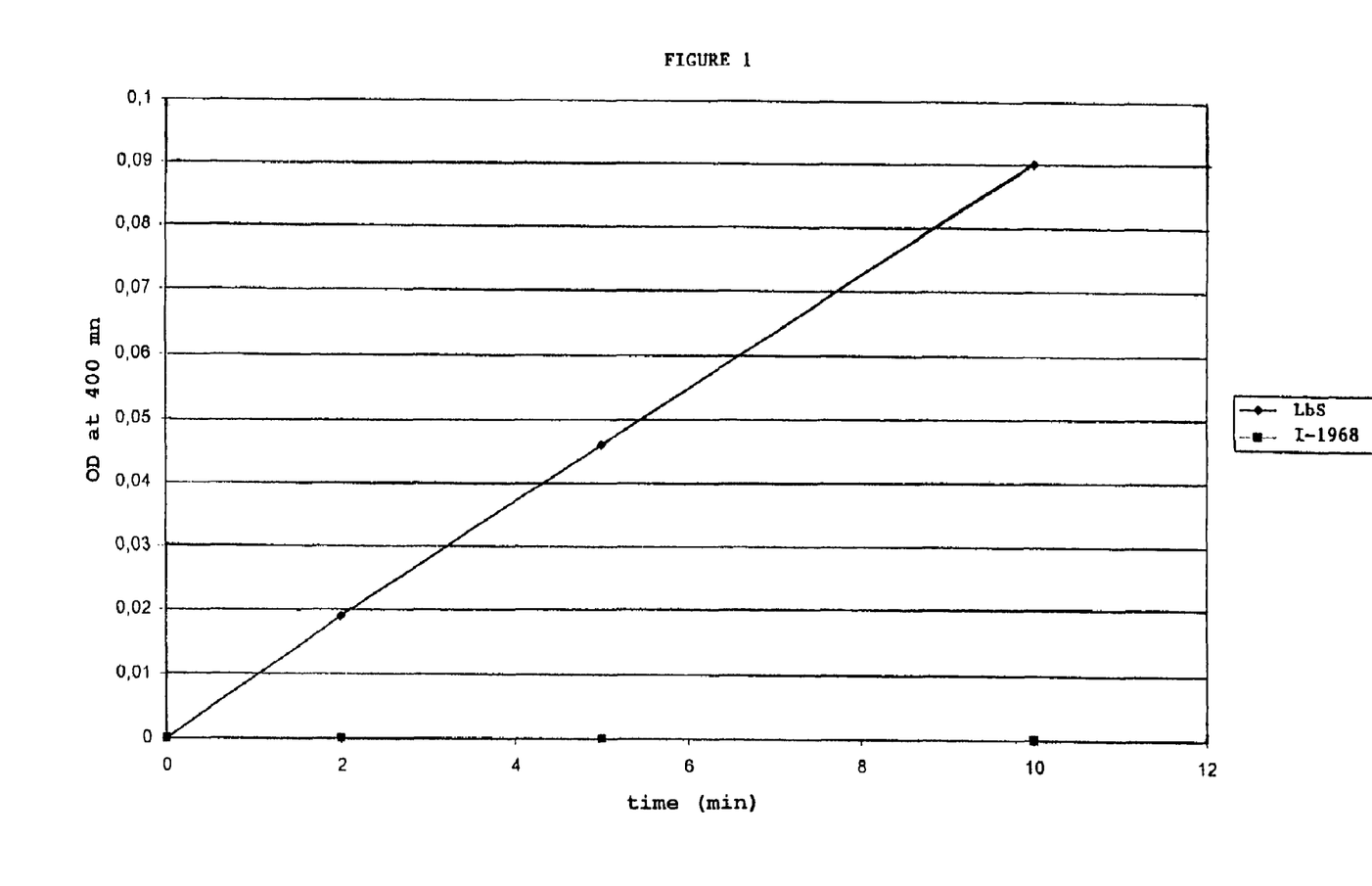
FIG. 1 is a graph showing the galactosidase activities of the LbS parent strain and of the I-1968 mutant in accordance with the invention, measured as a function of time.

The galactosidase activities of the LbS parent strain and of the I-1968 mutant in accordance with the invention, measured as a function of time, are given in FIG. 1.

These results show that the β-galactosidase is totally inactive in the mutant in accordance with the invention.

Example 2

Stability of the I-1968 Mutant of L. bulgaricus

The stability of the I-1968 mutant was tested in media containing, as carbon sources, either a mixture of glucose and of lactose, or lactose only.

An I-1968 culture obtained on MRS medium containing glucose is subcultured on sterilized milk which is supplemented with yeast autolyzate (2 g/l) and which may or may not be supplemented with glucose (20 g/l). When a pH of 5.2 (coagulation of the milk) is reached, samples of each subculturing are taken, on which the capacity of the bacteria to ferment sugars, as well as the presence of β-galactosidase activity (X-gal plate assay: white colonies=β-galactosidase minus; blue colonies=β-galactosidase plus), and analyzed.

The results are given in Table I below.

TABLE I

| Medium | Milk + glucose (20 g/l) | Milk |
|---|---|---|
| Time to reach pH 5.2 | 6 h00 | 20 h00 |
| Fermentation of sugars | glucose, fructose, mannose | lactose, glucose, fructose, mannose |
| X-gal plate assay | 100% white colonies | 20% white colonies 80% blue colonies |

These results show that, in the presence of glucose, the I-1968 strain does not revert toward a strain capable of using lactose. Conversely, in a medium-containing lactose as the only carbon source, rapid reversion of the I-1968 strain toward the original state is observed.

Example 3

Acidification, Postacidification and Survival Properties of the I-1968 Variant of L. bulgaricus in Symbiosis With S. thermophilus: The Case of a Method for Manufacturing a Set Yogurt (Fermentation in a Ventilated Oven)

Yogurt ferments are prepared combining the I-1968 strain in accordance with the invention with various industrial strains of S. thermophilus (the strains of S. thermophilus used are hereafter termed ST1, ST2 and ST3).

By way of comparison, the ferments are prepared combining the LbS parent strain and the same strains of S. thermophilus.

For preparing the ferments, the strains are seeded separately, and at 1% on the following composition:
Composition for 1 Liter:
135 g of skimmed milk powder
2 g of yeast autolyzate
920 ml of distilled water
20 g of glucose (for the I-1968 strain only)
Hydration: 10 min
Pasteurization: 30 min at 95° C.

The milk is then cooled to 44° C. and inoculated, and then incubated at 44° C. until an acidity of 85° D (degrees Dornic) for the streptococci and of 80° D for the lactobacilli is obtained.

The cultures are then cooled so as to obtain a ferment consisting of 80% Streptococcus thermophilus and of 20% Lactobacillus bulgaricus.

The ferments thus obtained are used to inoculate the following preparation:
Composition for 1 Liter:
99% of milk
0, 1, or 2 g/l of glucose
Hydration: 10 min
Pasteurization: 10 min at 95° C.

The milk is then cooled to 44° C. and inoculated at 1%.

For each experiment, the composition of the ferment and the amount of glucose added are given in Table II below:

TABLE II

| Experiment | Glucose g/l | Strains | Percentage |
|---|---|---|---|
| 1 | 0 | ST 3 | 64% |
|  |  | ST 2 | 16% |
|  |  | LbS | 20% |

TABLE II-continued

| Experiment | Glucose g/l | Strains | Percentage |
|---|---|---|---|
| 2 | 0 | ST 3 | 64% |
|  |  | ST 2 | 16% |
|  |  | I-1968 | 20% |
| 3 | 1 | ST 3 | 64% |
|  |  | ST 2 | 16% |
|  |  | I-1968 | 20% |
| 4 | 0 | ST 1 | 80% |
|  |  | LbS | 20% |
| 5 | 0 | ST 1 | 80% |
|  |  | I-1968 | 20% |
| 6 | 2 | ST 1 | 80% |
|  |  | I-1968 | 20% |

After inoculation, the milk is distributed into round-bottomed flasks and incubated at a temperature of 44° C. The acidification profile is monitored during the incubation. The products are uncurdled at pH 4.6 by cooling in a cold unit (16 hours at 4° C.).

The products are then subjected to a conservation test at 10° C. In this test, the pH and Dornic acidity are measured after 1, 14, 21 and 28 days of conservation.

The acidification results (time to reach a pH of 4.6 and pH value at 24 h) are given in Table III below:

TABLE III

| Experiment | Time to reach pH 4.6 (min) | Time to reach pH 4.5 (min) | pH at 24 h |
|---|---|---|---|
| 1 | 215 | 236 | 3.67 |
| 2 | 550 | 778 | 4.33 |
| 3 | 416 | 507 | 4.26 |
| 4 | 225 | 241 | 3.67 |
| 5 | 660 | >1500 | 4.54 |
| 6 | 390 | 465 | 4.35 |

The results of the conservation test at 10° C. (monitoring of the pH and of the Dornic acidity) and the survival test (*S. thermophilus* and *L. bulgaricus* populations) at 28 days are given in Table IV below:

TABLE IV

| Experiment | Storage time (days) | pH | Dornic acidity | Streptococcus thermophilus cells/ml | Lactobacillus bulgaricus cells/ml |
|---|---|---|---|---|---|
| 1 | 1 | 4.41 | 101 | 7.25E+08 | 3.35E+08 |
| 1 | 14 | 3.98 | 140 | ND | ND |
| 1 | 21 | 3.95 | 145 | ND | ND |
| 1 | 28 | 3.9 | 148 | 7.35E+08 | 3.30E+08 |
| 2 | 1 | 4.5 | 93 | 5.60E+08 | 2.90E+07 |
| 2 | 14 | 4.23 | 110 | Nd | ND |
| 2 | 21 | 4.18 | 112 | ND | ND |
| 2 | 28 | 4.19 | 114 | 5.65E+08 | 1.87E+07 |
| 3 | 1 | 4.49 | 96 | 6.90E+08 | 7.45E+07 |
| 3 | 14 | 4.14 | 115 | ND | ND |
| 3 | 21 | 4.15 | 117 | ND | ND |
| 3 | 28 | 4.15 | 120 | 8.65E+08 | 6.30E+07 |
| 4 | 1 | 4.39 | 105 | 6.30E+07 | 4.40E+08 |
| 4 | 14 | 3.91 | 145 | ND | ND |
| 4 | 21 | 3.9 | 151 | ND | ND |
| 4 | 28 | 3.85 | 157 | 4.70E+08 | 6.30E+08 |
| 5 | 1 | 4.6 | 85 | 9.05E+08 | 6.70E+07 |
| 5 | 14 | 4.58 | 80 | ND | ND |
| 5 | 21 | 4.53 | 80 | ND | ND |
| 5 | 28 | 4.61 | 79 | 9.40E+08 | 7.00E+07 |
| 6 | 1 | 4.51 | 89 | 1.05E+09 | 1.96E+08 |
| 6 | 14 | 4.38 | 90 | ND | ND |
| 6 | 21 | 4.39 | 96 | ND | ND |
| 6 | 28 | 4.42 | 90 | 1.62E+09 | 1.91E+08 |

ND = Not Determined

These results show that the yogurts produced using the symbioses combining the I-1968 strain with one or two strains of *S. thermophilus* show extremely reduced post-acidification with respect to the same symbioses with the LbS parent strain, while at the same time conserving an abundant population at the end of fermentation and good survival for 28 days at 10° C.

Stopping the acidification and maintaining the pH at around 4.6 to 4.5 for at least 24 hours at 44° C. makes it possible, in the context of manufacturing stirred yogurt, to reduce or even eliminate the phase of cooling in a tank, which is conventionally used.

That which is claimed is:

1. A mutant strain of *L. bulgaricus* lacking β-galactosidase activity, wherein said mutant strain carries a non-sense mutation in the sequence encoding β-galactosidase, and wherein said mutant strain grows and acidifies in milk are much more slowly than the wild-type strain from which it is derived, except when the milk is supplemented with at least one sugar which can be assimilated by said mutant strain.

2. The mutant strain of *L. bulgaricus* as claimed in claim 1, wherein said sugar which can be assimilated is glucose.

3. The mutant strain of claim 1, wherein said mutant strain grows and acidifies in milk at least two times more slowly than the wild-type strain from which it is derived, except when the milk is supplemented with at least one sugar which can be assimilated by said mutant strain.

4. A lactic ferment, which comprises at least one strain of *L. bulgaricus* as claimed in claim 1.

5. The lactic ferment as claimed in claim 4, wherein said strain of *L. bulgaricus* is combined with at least one strain of *S. thermophilus*.

6. A method for preparing a fermented dairy product, which comprises a step during which milk is fermented using a lactic ferment according to claim 4, in the presence of at least one sugar which can be assimilated by said mutant strain.

7. The method as claimed in claim 6, wherein said sugar which can be assimilated by said mutant strain is glucose.

8. The method as claimed in claim 6, wherein the arrest of fermentation is carried out without cooling of said dairy product.

9. A fermented dairy product obtained using a method as claimed in claim 6.

10. The fermented dairy product as claimed in claim 9, wherein said product is a yogurt.

* * * * *

SEQUENCE LISTING

```
<160> NUMBER OF SEQ ID NOS: 3

<210> SEQ ID NO 1
<211> LENGTH: 5059
<212> TYPE: DNA
<213> ORGANISM: Lactobacillus bulgaricus
<220> FEATURE:
<221> NAME/KEY: CDS
<222> LOCATION: (122)..(1873)
<220> FEATURE:
<221> NAME/KEY: CDS
<222> LOCATION: (1877)..(4519)

<400> SEQUENCE: 1
gcttgtctca cgcttgtcgt acgcggccgg tgcctttggc aacgacgtct tctacgcgac      60
tctgtcaacc tactttatcg tcttcgtcac cacccacctc tttaatgccg gtgaccacaa     120 g atg atc ttt atc atc acc aac ttg atc acc gcc atc cgg atc ggg gaa    169
```

-continued

```
    Met Ile Phe Ile Ile Thr Asn Leu Ile Thr Ala Ile Arg Ile Gly Glu
     1               5                  10                  15 gtc ctg ctc gac ccc ttg atc ggt aac gcc atc gac cgg acc gaa agc        217
Val Leu Leu Asp Pro Leu Ile Gly Asn Ala Ile Asp Arg Thr Glu Ser
                 20                  25                  30 cgg tgg ggg aag ttc aag ccc tgg gtt gtg ggc ggg ggg atc atc agc        265
Arg Trp Gly Lys Phe Lys Pro Trp Val Val Gly Gly Gly Ile Ile Ser
         35                  40                  45 tca tta gcc ctc tta gcc ctc ttt acc gac ttt ggc ggc att aac caa        313
Ser Leu Ala Leu Leu Ala Leu Phe Thr Asp Phe Gly Gly Ile Asn Gln
     50                  55                  60 agc aac ccc gtt gtt tac tta gta atc ttc ggt att gtt tac ttg att        361
Ser Asn Pro Val Val Tyr Leu Val Ile Phe Gly Ile Val Tyr Leu Ile
 65                  70                  75                  80 atg gat atc ttc tac tca ttt aaa gac act ggc ttc tgg gcc atg atc        409
Met Asp Ile Phe Tyr Ser Phe Lys Asp Thr Gly Phe Trp Ala Met Ile
                 85                  90                  95 ccg gcc ttg tcc ctg gat tcc cgg gaa aga gag aag acc tcc acc ttc        457
Pro Ala Leu Ser Leu Asp Ser Arg Glu Arg Glu Lys Thr Ser Thr Phe
             100                 105                 110 gcc aga gtc ggc tcc acc atc ggg gcc aac ctg gtc ggg gta gtc atc        505
Ala Arg Val Gly Ser Thr Ile Gly Ala Asn Leu Val Gly Val Val Ile
         115                 120                 125 acc cca atc atc ctc ttc ttc tcg gcc agc aag gcc aac ccc aac ggg        553
Thr Pro Ile Ile Leu Phe Phe Ser Ala Ser Lys Ala Asn Pro Asn Gly
     130                 135                 140 gat aag cag ggc tgg ttc ttc ttt gcc ttg atc gtg gcc att gtc ggc        601
Asp Lys Gln Gly Trp Phe Phe Phe Ala Leu Ile Val Ala Ile Val Gly
145                 150                 155                 160 atc ttg acc tca att acc gtt ggt ctt ggt act cac gaa gta aaa tcc        649
Ile Leu Thr Ser Ile Thr Val Gly Leu Gly Thr His Glu Val Lys Ser
                 165                 170                 175 gcc ctg cgg gaa agc aat gaa aag acc act ttg aag cag gtc ttt aag        697
Ala Leu Arg Glu Ser Asn Glu Lys Thr Thr Leu Lys Gln Val Phe Lys
             180                 185                 190 gtc ctg ggg caa aac gac cag ctc ctc tgg ctg gcc ttt gcc tac tgg        745
Val Leu Gly Gln Asn Asp Gln Leu Leu Trp Leu Ala Phe Ala Tyr Trp
         195                 200                 205 ttt tac ggc ctg ggt atc aac acc ctg aac gct ctg caa ctt tac tac        793
Phe Tyr Gly Leu Gly Ile Asn Thr Leu Asn Ala Leu Gln Leu Tyr Tyr
     210                 215                 220 ttc tca tac atc tta ggc gat gcc cgc ggc tac agc ctg ctt tac acc        841
Phe Ser Tyr Ile Leu Gly Asp Ala Arg Gly Tyr Ser Leu Leu Tyr Thr
225                 230                 235                 240 atc aac acc ttt gtc ggt tta atc tct gca tcc ttc ttc cca tca ctg        889
Ile Asn Thr Phe Val Gly Leu Ile Ser Ala Ser Phe Phe Pro Ser Leu
                 245                 250                 255 gcc aag aag ttc aac aga aat cgc ctc ttc tac gcc tgc atc gcg gtg        937
Ala Lys Lys Phe Asn Arg Asn Arg Leu Phe Tyr Ala Cys Ile Ala Val
             260                 265                 270 atg ctg tta ggg atc ggg gtc ttc tcc gtg gcc agc ggt tct ctg gcc        985
Met Leu Leu Gly Ile Gly Val Phe Ser Val Ala Ser Gly Ser Leu Ala
         275                 280                 285 ctg tcc ctt gtt ggg gca gaa ttc ttc ttt att ccg cag cct ctg gcc       1033
Leu Ser Leu Val Gly Ala Glu Phe Phe Phe Ile Pro Gln Pro Leu Ala
     290                 295                 300 ttc ctg gtc gtt ttg atg atc atc tct gac gct gtt gaa tac ggc cag       1081
Phe Leu Val Val Leu Met Ile Ile Ser Asp Ala Val Glu Tyr Gly Gln
305                 310                 315                 320
```

-continued

| | |
|---|---|
| ctg aaa act ggc cac aga gac gaa gct ttg acc ctg tct gtc cgg cca<br>Leu Lys Thr Gly His Arg Asp Glu Ala Leu Thr Leu Ser Val Arg Pro<br>   325     330     335 | 1129 |
| ttg gtc gat aag ctg ggc ggg gcc ttg tcc aac tgg ttt gtt tcc ttg<br>Leu Val Asp Lys Leu Gly Gly Ala Leu Ser Asn Trp Phe Val Ser Leu<br>   340     345     350 | 1177 |
| att gcc tta act gcc ggc atg acc act ggg gcg act gcc tca aca att<br>Ile Ala Leu Thr Ala Gly Met Thr Thr Gly Ala Thr Ala Ser Thr Ile<br> 355     360     365 | 1225 |
| aca gct cat ggc cag atg gtc ttc aag tta gct atg ttt gcc tta ccg<br>Thr Ala His Gly Gln Met Val Phe Lys Leu Ala Met Phe Ala Leu Pro<br>370     375     380 | 1273 |
| gca gtc atg ctc ttg atc gct gtt tct att ttc gcc aaa aag gtc ttc<br>Ala Val Met Leu Leu Ile Ala Val Ser Ile Phe Ala Lys Lys Val Phe<br>385     390     395     400 | 1321 |
| ttg act gaa gaa aag cac gcg gaa atc gtc gac cag ctg gaa act caa<br>Leu Thr Glu Glu Lys His Ala Glu Ile Val Asp Gln Leu Glu Thr Gln<br>   405     410     415 | 1369 |
| ttc agc caa agc cat gcc caa aag ccg gcg caa gct gaa agc ttc act<br>Phe Ser Gln Ser His Ala Gln Lys Pro Ala Gln Ala Glu Ser Phe Thr<br>   420     425     430 | 1417 |
| ttg gcc agc cca gtc tcc gga caa tta atg aac ctg gac atg gtt gac<br>Leu Ala Ser Pro Val Ser Gly Gln Leu Met Asn Leu Asp Met Val Asp<br>   435     440     445 | 1465 |
| gac ccg gtc ttt gcc gac aaa aag tta ggc gac ggc ttt gcc ctg gtg<br>Asp Pro Val Phe Ala Asp Lys Lys Leu Gly Asp Gly Phe Ala Leu Val<br>   450     455     460 | 1513 |
| cca gca gac ggt aag gtc tac gcg cca ttt gcc ggt act gtc cgc cag<br>Pro Ala Asp Gly Lys Val Tyr Ala Pro Phe Ala Gly Thr Val Arg Gln<br>465     470     475     480 | 1561 |
| ctg gcc aag acc cgg cac tcg atc gtc ctg gaa aat gaa cat ggg gtc<br>Leu Ala Lys Thr Arg His Ser Ile Val Leu Glu Asn Glu His Gly Val<br>   485     490     495 | 1609 |
| ttg gtc ttg att cac ctt ggc ctg ggc acg gtc aaa tta aac ggg act<br>Leu Val Leu Ile His Leu Gly Leu Gly Thr Val Lys Leu Asn Gly Thr<br>   500     505     510 | 1657 |
| ggc ttt gtc agc tat gtt gaa gag ggc agc cag gta gaa gcc ggc cag<br>Gly Phe Val Ser Tyr Val Glu Glu Gly Ser Gln Val Glu Ala Gly Gln<br>   515     520     525 | 1705 |
| cag atc ctg gaa ttc tgg gac ccg gcg atc aag cag gcc aag ctg gac<br>Gln Ile Leu Glu Phe Trp Asp Pro Ala Ile Lys Gln Ala Lys Leu Asp<br>   530     535     540 | 1753 |
| gac acg gta atc gtg acc gtc atc aac agc gaa act ttc gca aat agc<br>Asp Thr Val Ile Val Thr Val Ile Asn Ser Glu Thr Phe Ala Asn Ser<br>545     550     555     560 | 1801 |
| cag atg ctc ttg ccg atc ggc cac agc gtc caa gcc ctg gat gat gta<br>Gln Met Leu Leu Pro Ile Gly His Ser Val Gln Ala Leu Asp Asp Val<br>   565     570     575 | 1849 |
| ttc aag tta gaa ggg aag aat tag aaa atg agc aat aag tta gta aaa<br>Phe Lys Leu Glu Gly Lys Asn    Met Ser Asn Lys Leu Val Lys<br>   580         585     590 | 1897 |
| gaa aaa aga gtt gac cag gca gac ttg gcc tgg ctg act gac ccg gaa<br>Glu Lys Arg Val Asp Gln Ala Asp Leu Ala Trp Leu Thr Asp Pro Glu<br>   595     600     605 | 1945 |
| gtt tac gaa gtc aat aca att ccc ccg cac tcc gac cat gag tcc ttc<br>Val Tyr Glu Val Asn Thr Ile Pro Pro His Ser Asp His Glu Ser Phe<br>   610     615     620 | 1993 |
| caa agc cag gaa gaa ctg gag gag ggc aag tcc agt tta gtg cag tcc<br>Gln Ser Gln Glu Glu Leu Glu Glu Gly Lys Ser Ser Leu Val Gln Ser<br>625     630     635 | 2041 |

| | | | | | | | | | | | | | | | | |
|---|---|---|---|---|---|---|---|---|---|---|---|---|---|---|---|---|
| ctg | gac | ggg | gac | tgg | ctg | att | gac | tac | gct | gaa | aac | ggc | cag | gga | cca | 2089 |
| Leu | Asp | Gly | Asp | Trp | Leu | Ile | Asp | Tyr | Ala | Glu | Asn | Gly | Gln | Gly | Pro | |
| 640 | | | | 645 | | | | 650 | | | | | 655 | | | |
| gtc | aac | ttc | tat | gca | gaa | gac | ttt | gac | gat | agc | aat | ttt | aag | tca | gtc | 2137 |
| Val | Asn | Phe | Tyr | Ala | Glu | Asp | Phe | Asp | Asp | Ser | Asn | Phe | Lys | Ser | Val | |
| | | | | 660 | | | | | 665 | | | | 670 | | | |
| aaa | gta | ccc | ggc | aac | ctg | gaa | ctg | caa | ggc | ttt | ggc | cag | ccc | cag | tat | 2185 |
| Lys | Val | Pro | Gly | Asn | Leu | Glu | Leu | Gln | Gly | Phe | Gly | Gln | Pro | Gln | Tyr | |
| | | | 675 | | | | | 680 | | | | | 685 | | | |
| gtc | aac | gtc | caa | tat | cca | tgg | gac | ggc | agt | gag | gag | att | ttc | ccg | ccc | 2233 |
| Val | Asn | Val | Gln | Tyr | Pro | Trp | Asp | Gly | Ser | Glu | Glu | Ile | Phe | Pro | Pro | |
| | | | | 690 | | | | 695 | | | | | 700 | | | |
| caa | att | cca | agc | aaa | aat | ccg | ctc | gct | tct | tat | gtc | aga | tac | ttt | gac | 2281 |
| Gln | Ile | Pro | Ser | Lys | Asn | Pro | Leu | Ala | Ser | Tyr | Val | Arg | Tyr | Phe | Asp | |
| | | | | 705 | | | | | 710 | | | | 715 | | | |
| ctg | gat | gaa | gct | ttc | tgg | gac | aag | gaa | gtc | agc | ttg | aag | ttt | gac | ggg | 2329 |
| Leu | Asp | Glu | Ala | Phe | Trp | Asp | Lys | Glu | Val | Ser | Leu | Lys | Phe | Asp | Gly | |
| 720 | | | | | 725 | | | | 730 | | | | | 735 | | |
| gcg | gca | aca | gcc | atc | tat | gtc | tgg | ctg | aac | ggc | cac | ttc | gtc | ggc | tac | 2377 |
| Ala | Ala | Thr | Ala | Ile | Tyr | Val | Trp | Leu | Asn | Gly | His | Phe | Val | Gly | Tyr | |
| | | | | 740 | | | | | 745 | | | | 750 | | | |
| ggg | gaa | gac | tcc | ttt | acc | cca | agc | gag | ttt | atg | gtt | acc | aag | ttc | ctc | 2425 |
| Gly | Glu | Asp | Ser | Phe | Thr | Pro | Ser | Glu | Phe | Met | Val | Thr | Lys | Phe | Leu | |
| | | | 755 | | | | | 760 | | | | | 765 | | | |
| aag | aaa | gaa | aat | aac | cgc | ctg | gca | gtg | gct | ctc | tac | aag | tat | tct | tcc | 2473 |
| Lys | Lys | Glu | Asn | Asn | Arg | Leu | Ala | Val | Ala | Leu | Tyr | Lys | Tyr | Ser | Ser | |
| | | | | 770 | | | | | 775 | | | | 780 | | | |
| gcc | tcc | tgg | ctg | gaa | gac | cag | gac | ttc | tgg | cgc | atg | tct | ggt | ttg | ttc | 2521 |
| Ala | Ser | Trp | Leu | Glu | Asp | Gln | Asp | Phe | Trp | Arg | Met | Ser | Gly | Leu | Phe | |
| 785 | | | | | 790 | | | | 795 | | | | | | | |
| aga | tca | gtg | act | ctt | cag | gcc | aag | ccg | cgt | ctg | cac | ttg | gag | gac | ctt | 2569 |
| Arg | Ser | Val | Thr | Leu | Gln | Ala | Lys | Pro | Arg | Leu | His | Leu | Glu | Asp | Leu | |
| 800 | | | | | 805 | | | | | 810 | | | | | 815 | |
| aag | ctt | acg | gcc | agc | ttg | acc | gat | aac | tac | caa | aaa | gga | aag | ctg | gaa | 2617 |
| Lys | Leu | Thr | Ala | Ser | Leu | Thr | Asp | Asn | Tyr | Gln | Lys | Gly | Lys | Leu | Glu | |
| | | | | 820 | | | | | 825 | | | | | 830 | | |
| gtc | gaa | gcc | aat | att | gcc | tac | cgc | ttg | cca | aat | gcc | agc | ttt | aag | ctg | 2665 |
| Val | Glu | Ala | Asn | Ile | Ala | Tyr | Arg | Leu | Pro | Asn | Ala | Ser | Phe | Lys | Leu | |
| | | | | 835 | | | | | 840 | | | | 845 | | | |
| gaa | gtg | cgg | gat | agt | gaa | ggt | gac | ttg | gtt | gct | gaa | aag | ctg | ggc | cca | 2713 |
| Glu | Val | Arg | Asp | Ser | Glu | Gly | Asp | Leu | Val | Ala | Glu | Lys | Leu | Gly | Pro | |
| | | 850 | | | | | 855 | | | | | 860 | | | | |
| atc | aga | agc | gag | cag | ctg | gaa | ttc | act | ctg | gct | gat | ttg | cca | gta | gct | 2761 |
| Ile | Arg | Ser | Glu | Gln | Leu | Glu | Phe | Thr | Leu | Ala | Asp | Leu | Pro | Val | Ala | |
| 865 | | | | | 870 | | | | | 875 | | | | | | |
| gcc | tgg | agc | gcg | gaa | aag | cct | aac | ctt | tac | cag | gtc | cgc | ctg | tat | tta | 2809 |
| Ala | Trp | Ser | Ala | Glu | Lys | Pro | Asn | Leu | Tyr | Gln | Val | Arg | Leu | Tyr | Leu | |
| 880 | | | | | 885 | | | | | 890 | | | | | 895 | |
| tac | cag | gca | ggc | agc | ctc | tta | gag | gtt | agc | cgg | cag | gaa | gtg | ggt | ttc | 2857 |
| Tyr | Gln | Ala | Gly | Ser | Leu | Leu | Glu | Val | Ser | Arg | Gln | Glu | Val | Gly | Phe | |
| | | | | 900 | | | | | 905 | | | | | 910 | | |
| cgc | aac | ttt | gaa | cta | aaa | gac | ggg | att | atg | tac | ctt | aac | ggc | cag | cgg | 2905 |
| Arg | Asn | Phe | Glu | Leu | Lys | Asp | Gly | Ile | Met | Tyr | Leu | Asn | Gly | Gln | Arg | |
| | | | | 915 | | | | | 920 | | | | 925 | | | |
| atc | gtc | ttc | aag | ggg | gcc | aac | cgg | cac | gaa | ttt | gac | agt | aag | ttg | ggc | 2953 |
| Ile | Val | Phe | Lys | Gly | Ala | Asn | Arg | His | Glu | Phe | Asp | Ser | Lys | Leu | Gly | |
| | | | 930 | | | | | 935 | | | | | 940 | | | |
| cgg | gct | atc | aca | gaa | gag | gat | atg | atc | tgg | gat | atc | aag | acc | atg | aag | 3001 |
| Arg | Ala | Ile | Thr | Glu | Glu | Asp | Met | Ile | Trp | Asp | Ile | Lys | Thr | Met | Lys | |

-continued

```
                945                 950                 955 cga agc aac atc aat gct gtc cgc tgc tct cac tac ccg aac cag tcc    3049
Arg Ser Asn Ile Asn Ala Val Arg Cys Ser His Tyr Pro Asn Gln Ser
960                 965                 970                 975 ctc ttt tac cgg ctc tgt gac aag tac ggc ctt tac gtc att gat gaa    3097
Leu Phe Tyr Arg Leu Cys Asp Lys Tyr Gly Leu Tyr Val Ile Asp Glu
            980                 985                 990 gct aac ctg gaa agc cac ggc acc tgg gaa aaa gtg ggg ggg cac gaa    3145
Ala Asn Leu Glu Ser His Gly Thr Trp Glu Lys Val Gly Gly His Glu
        995                 1000                1005 gat cct agc ttc aat gtt cca ggc gat gac cag cat tgg ctg gga gcc    3193
Asp Pro Ser Phe Asn Val Pro Gly Asp Asp Gln His Trp Leu Gly Ala
    1010                1015                1020 agc tta tcc cgg gtg aag aac atg atg gct cgg gac aag aac cat gct    3241
Ser Leu Ser Arg Val Lys Asn Met Met Ala Arg Asp Lys Asn His Ala
1025                1030                1035 tca atc ctg atc tgg tct tta ggc aat gag tct tac gcc ggc act gtc    3289
Ser Ile Leu Ile Trp Ser Leu Gly Asn Glu Ser Tyr Ala Gly Thr Val
1040                1045                1050                1055 ttt gcc caa atg gct gat tac gtc cgg aag gct gat ccg acc cgg gtt    3337
Phe Ala Gln Met Ala Asp Tyr Val Arg Lys Ala Asp Pro Thr Arg Val
                1060                1065                1070 cag cac tat gaa ggg gtg acc cac aac cgg aag ttt gac gac gcc acc    3385
Gln His Tyr Glu Gly Val Thr His Asn Arg Lys Phe Asp Asp Ala Thr
            1075                1080                1085 cag att gaa agc cgg atg tat gct ccg gcc aag gta att gaa gaa tac    3433
Gln Ile Glu Ser Arg Met Tyr Ala Pro Ala Lys Val Ile Glu Glu Tyr
        1090                1095                1100 ttg acc aat aaa cca gcc aag cca ttt atc tca gtt gaa tac gct cac    3481
Leu Thr Asn Lys Pro Ala Lys Pro Phe Ile Ser Val Glu Tyr Ala His
    1105                1110                1115 gcc atg ggc aac tcc gtc ggt gac ctg gcc gcc tac acg gcc ctg gaa    3529
Ala Met Gly Asn Ser Val Gly Asp Leu Ala Ala Tyr Thr Ala Leu Glu
1120                1125                1130                1135 aaa tac ccc cac tac cag ggc ggc ttc atc tgg gac tgg att gac caa    3577
Lys Tyr Pro His Tyr Gln Gly Gly Phe Ile Trp Asp Trp Ile Asp Gln
                1140                1145                1150 gga ctg gaa aaa gac ggg cac ctg ctt tat ggg ggc gac ttc gat gac    3625
Gly Leu Glu Lys Asp Gly His Leu Leu Tyr Gly Gly Asp Phe Asp Asp
            1155                1160                1165 cgg cca acc gac tat gaa ttc tgc ggg aac ggc ctg gtc ttt gct gac    3673
Arg Pro Thr Asp Tyr Glu Phe Cys Gly Asn Gly Leu Val Phe Ala Asp
        1170                1175                1180 cgg act gaa tcg ccg aaa ctg gct aat gtc aag gcc ctt tac gcc aac    3721
Arg Thr Glu Ser Pro Lys Leu Ala Asn Val Lys Ala Leu Tyr Ala Asn
    1185                1190                1195 ctt aag tta gaa gta aaa gat ggg cag ctc ttc ctc aaa aac gac aat    3769
Leu Lys Leu Glu Val Lys Asp Gly Gln Leu Phe Leu Lys Asn Asp Asn
1200                1205                1210                1215 tta ttt acc aac agc tca tct tac tac ttc ttg act agt ctt ttg gtc    3817
Leu Phe Thr Asn Ser Ser Ser Tyr Tyr Phe Leu Thr Ser Leu Leu Val
                1220                1225                1230 gat ggc aag ttg acc tac cag agc cgg cct ctg acc ttt ggc ctg gag    3865
Asp Gly Lys Leu Thr Tyr Gln Ser Arg Pro Leu Thr Phe Gly Leu Glu
            1235                1240                1245 cct ggc gaa tcc ggg acc ttt gcc ctg cct tgg ccg gaa gtc gct gat    3913
Pro Gly Glu Ser Gly Thr Phe Ala Leu Pro Trp Pro Glu Val Ala Asp
        1250                1255                1260 gaa aaa gga gag gtc gtc tac cgg gta acg gcc cac tta aaa gaa gac    3961
```

```
                Glu Lys Gly Glu Val Val Tyr Arg Val Thr Ala His Leu Lys Glu Asp
                1265                1270                1275 ttg cct tgg gcg gat gag ggc ttc act gtg gct gaa gca gaa gaa gta        4009
Leu Pro Trp Ala Asp Glu Gly Phe Thr Val Ala Glu Ala Glu Glu Val
1280                1285                1290                1295 gct caa aag ctg ccg gaa ttt aag ccg gaa ggg cgg cca gat tta gtt        4057
Ala Gln Lys Leu Pro Glu Phe Lys Pro Glu Gly Arg Pro Asp Leu Val
            1300                1305                1310 gat tcc gac tac aac cta ggc ctg aaa gga aat aac ttc caa att ctc        4105
Asp Ser Asp Tyr Asn Leu Gly Leu Lys Gly Asn Asn Phe Gln Ile Leu
        1315                1320                1325 ttc tcc aag gtc aag ggc tgg ccg gtt tcc ctc aag tat gcc ggt agg        4153
Phe Ser Lys Val Lys Gly Trp Pro Val Ser Leu Lys Tyr Ala Gly Arg
    1330                1335                1340 gaa tac ttg aag cgg ctg ccg gaa ttt acc ttc tgg cgg gcc ctg acg        4201
Glu Tyr Leu Lys Arg Leu Pro Glu Phe Thr Phe Trp Arg Ala Leu Thr
1345                1350                1355 gac aac gac cgg gga gct ggt tac ggc tat gat ctg gcc cgg tgg gaa        4249
Asp Asn Asp Arg Gly Ala Gly Tyr Gly Tyr Asp Leu Ala Arg Trp Glu
1360                1365                1370                1375 aat gcc ggc aag tat gcc cgc ttg aaa gac atc agc tgc gag gtc aag        4297
Asn Ala Gly Lys Tyr Ala Arg Leu Lys Asp Ile Ser Cys Glu Val Lys
            1380                1385                1390 gaa gac tcc gtt ttg gtc aag act gcc ttt acg ttg cct gtc gcc tta        4345
Glu Asp Ser Val Leu Val Lys Thr Ala Phe Thr Leu Pro Val Ala Leu
        1395                1400                1405 aag ggt gat tta act gtg acc tat gaa gtc gat gga cgg ggc aag att        4393
Lys Gly Asp Leu Thr Val Thr Tyr Glu Val Asp Gly Arg Gly Lys Ile
    1410                1415                1420 gct gta aca gct gac ttc cca ggc gcg gaa gaa gcc ggt ctc ttg cca        4441
Ala Val Thr Ala Asp Phe Pro Gly Ala Glu Glu Ala Gly Leu Leu Pro
1425                1430                1435 gcc ttt ggc ttg aac ctg gcc ctg cca aaa gaa ctg acc gat tac cgc        4489
Ala Phe Gly Leu Asn Leu Ala Leu Pro Lys Glu Leu Thr Asp Tyr Arg
1440                1445                1450                1455 tac tat ggt ctg gga cct aat gag agc taa ccagaccgct tggaaggtaa         4539
Tyr Tyr Gly Leu Gly Pro Asn Glu Ser
            1460                1465 ttacctgggc atctaccagg gagcggtaaa aaagaacttt agcccatacc tgcgtccgca    4599
ggaaacgggc aaccggagca aggttcgctg gtaccagctc tttgatgaaa agggcggctt    4659
ggaatttacg gccaatgggg cagacttgaa cttgtctgct ttgccatatt ctgccgccca    4719
aattgaagca gcggaccacg cttttgaact gactaacaat tacacttggg ttagagcctt    4779
aagcgcccag atgggggtcg gcggggatga ctcctggggg cagaaggtcc acccggaatt    4839
ctgcctggat gctcaaaaag cccgccagct ccgcctggtg attcagcccc ttttactaaa    4899
ataaatgcta caattgactt aacaggatga aatttagta aaagcaaagc gagtgaggaa     4959
gatggcaacg atcagagaag tgccaaggca gccggcgtgt cgctagcgac ggtttcccgc    5019
gtcttgaact atgaccagac cctgtcagtc aatgaggcaa                          5059

<210> SEQ ID NO 2
<211> LENGTH: 583
<212> TYPE: PRT
<213> ORGANISM: Lactobacillus bulgaricus

<400> SEQUENCE: 2

Met Ile Phe Ile Ile Thr Asn Leu Ile Thr Ala Ile Arg Ile Gly Glu
 1               5                  10                  15
```

```
Val Leu Leu Asp Pro Leu Ile Gly Asn Ala Ile Asp Arg Thr Glu Ser
             20                  25                  30

Arg Trp Gly Lys Phe Lys Pro Trp Val Gly Gly Ile Ile Ser
         35                  40                  45

Ser Leu Ala Leu Leu Ala Leu Phe Thr Asp Phe Gly Gly Ile Asn Gln
             50                  55                  60

Ser Asn Pro Val Val Tyr Leu Val Ile Phe Gly Ile Val Tyr Leu Ile
 65                  70                  75                  80

Met Asp Ile Phe Tyr Ser Phe Lys Asp Thr Gly Phe Trp Ala Met Ile
                 85                  90                  95

Pro Ala Leu Ser Leu Asp Ser Arg Glu Arg Glu Lys Thr Ser Thr Phe
            100                 105                 110

Ala Arg Val Gly Ser Thr Ile Gly Ala Asn Leu Val Gly Val Val Ile
            115                 120                 125

Thr Pro Ile Ile Leu Phe Phe Ser Ala Ser Lys Ala Asn Pro Asn Gly
        130                 135                 140

Asp Lys Gln Gly Trp Phe Phe Ala Leu Ile Val Ala Ile Val Gly
145                 150                 155                 160

Ile Leu Thr Ser Ile Thr Val Gly Leu Gly Thr His Glu Val Lys Ser
                165                 170                 175

Ala Leu Arg Glu Ser Asn Glu Lys Thr Thr Leu Lys Gln Val Phe Lys
            180                 185                 190

Val Leu Gly Gln Asn Asp Gln Leu Leu Trp Leu Ala Phe Ala Tyr Trp
        195                 200                 205

Phe Tyr Gly Leu Gly Ile Asn Thr Leu Asn Ala Leu Gln Leu Tyr Tyr
    210                 215                 220

Phe Ser Tyr Ile Leu Gly Asp Ala Arg Gly Tyr Ser Leu Leu Tyr Thr
225                 230                 235                 240

Ile Asn Thr Phe Val Gly Leu Ile Ser Ala Ser Phe Phe Pro Ser Leu
                245                 250                 255

Ala Lys Lys Phe Asn Arg Asn Arg Leu Phe Tyr Ala Cys Ile Ala Val
            260                 265                 270

Met Leu Leu Gly Ile Gly Val Phe Ser Val Ala Ser Gly Ser Leu Ala
        275                 280                 285

Leu Ser Leu Val Gly Ala Glu Phe Phe Ile Pro Gln Pro Leu Ala
    290                 295                 300

Phe Leu Val Val Leu Met Ile Ile Ser Asp Ala Val Glu Tyr Gly Gln
305                 310                 315                 320

Leu Lys Thr Gly His Arg Asp Glu Ala Leu Thr Leu Ser Val Arg Pro
                325                 330                 335

Leu Val Asp Lys Leu Gly Gly Ala Leu Ser Asn Trp Phe Val Ser Leu
            340                 345                 350

Ile Ala Leu Thr Ala Gly Met Thr Thr Gly Ala Thr Ala Ser Thr Ile
        355                 360                 365

Thr Ala His Gly Gln Met Val Phe Lys Leu Ala Met Phe Ala Leu Pro
    370                 375                 380

Ala Val Met Leu Leu Ile Ala Val Ser Ile Phe Ala Lys Lys Val Phe
385                 390                 395                 400

Leu Thr Glu Glu Lys His Ala Glu Ile Val Asp Gln Leu Glu Thr Gln
                405                 410                 415

Phe Ser Gln Ser His Ala Gln Lys Pro Ala Gln Ala Glu Ser Phe Thr
            420                 425                 430
```

-continued

Leu Ala Ser Pro Val Ser Gly Gln Leu Met Asn Leu Asp Met Val Asp
        435                 440                 445

Asp Pro Val Phe Ala Asp Lys Lys Leu Gly Asp Gly Phe Ala Leu Val
        450                 455                 460

Pro Ala Asp Gly Lys Val Tyr Ala Pro Phe Ala Gly Thr Val Arg Gln
465                 470                 475                 480

Leu Ala Lys Thr Arg His Ser Ile Val Leu Glu Asn Glu His Gly Val
                485                 490                 495

Leu Val Leu Ile His Leu Gly Leu Gly Thr Val Lys Leu Asn Gly Thr
            500                 505                 510

Gly Phe Val Ser Tyr Val Glu Gly Ser Gln Val Glu Ala Gly Gln
        515                 520                 525

Gln Ile Leu Glu Phe Trp Asp Pro Ala Ile Lys Gln Ala Lys Leu Asp
    530                 535                 540

Asp Thr Val Ile Val Thr Val Ile Asn Ser Glu Thr Phe Ala Asn Ser
545                 550                 555                 560

Gln Met Leu Leu Pro Ile Gly His Ser Val Gln Ala Leu Asp Asp Val
                565                 570                 575

Phe Lys Leu Glu Gly Lys Asn
            580

<210> SEQ ID NO 3
<211> LENGTH: 880
<212> TYPE: PRT
<213> ORGANISM: Lactobacillus bulgaricus

<400> SEQUENCE: 3

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Met Ser Gly Leu Phe Arg Ser Val Thr Leu Gln Ala Lys Pro
    210                 215                 220

-continued

```
Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Leu Gly Pro Ile Arg Ser Glu Gln Leu Glu Phe Thr
        275                 280                 285

Leu Ala Asp Leu Pro Val Ala Ala Trp Ser Ala Glu Lys Pro Asn Leu
    290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
            340                 345                 350

Glu Phe Asp Ser Lys Leu Gly Arg Ala Ile Thr Glu Glu Asp Met Ile
        355                 360                 365

Trp Asp Ile Lys Thr Met Lys Arg Ser Asn Ile Asn Ala Val Arg Cys
    370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
            420                 425                 430

Asp Gln His Trp Leu Gly Ala Ser Leu Ser Arg Val Lys Asn Met Met
        435                 440                 445

Ala Arg Asp Lys Asn His Ala Ser Ile Leu Ile Trp Ser Leu Gly Asn
    450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
            500                 505                 510

Ala Lys Val Ile Glu Glu Tyr Leu Thr Asn Lys Pro Ala Lys Pro Phe
        515                 520                 525

Ile Ser Val Glu Tyr Ala His Ala Met Gly Asn Ser Val Gly Asp Leu
    530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
            580                 585                 590

Asn Gly Leu Val Phe Ala Asp Arg Thr Glu Ser Pro Lys Leu Ala Asn
        595                 600                 605

Val Lys Ala Leu Tyr Ala Asn Leu Lys Leu Glu Val Lys Asp Gly Gln
    610                 615                 620

Leu Phe Leu Lys Asn Asp Asn Leu Phe Thr Asn Ser Ser Ser Tyr Tyr
625                 630                 635                 640
```

-continued

```
Phe Leu Thr Ser Leu Leu Val Asp Gly Lys Leu Thr Tyr Gln Ser Arg
            645                 650                 655

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
            675                 680                 685

Thr Ala His Leu Lys Glu Asp Leu Pro Trp Ala Asp Glu Gly Phe Thr
            690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
            725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
            755                 760                 765

Thr Phe Trp Arg Ala Leu Thr Asp Asn Asp Arg Gly Ala Gly Tyr Gly
            770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
            805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala
            835                 840                 845

Glu Glu Ala Gly Leu Leu Pro Ala Phe Gly Leu Asn Leu Ala Leu Pro
            850                 855                 860

Lys Glu Leu Thr Asp Tyr Arg Tyr Gly Leu Gly Pro Asn Glu Ser
865                 870                 875                 880
```